(12) United States Patent
Blakesley et al.

(10) Patent No.: US 7,124,759 B2
(45) Date of Patent: Oct. 24, 2006

(54) BED MOUNTABLE RESTRAINING DEVICE AND METHOD FOR USING SAME

(75) Inventors: Shannon J. Blakesley, 2244 Casa Alta, Spring Valley, CA (US) 91977; Mark Tyler Blakesley, 2244 Casa Alta, Spring Valley, CA (US) 91977

(73) Assignees: Shannon J. Blakesley, Spring Valley, CA (US); Mark Tyler Blakesley, Spring Valley, CA (US)

( * ) Notice: Subject to any disclaimer, the term of this patent is extended or adjusted under 35 U.S.C. 154(b) by 118 days.

(21) Appl. No.: 10/976,579

(22) Filed: Oct. 29, 2004

(65) Prior Publication Data

US 2006/0090764 A1   May 4, 2006

(51) Int. Cl.
*A61B 19/00* (2006.01)

(52) U.S. Cl. ............... 128/869; 128/870; 128/845; 602/60

(58) Field of Classification Search ........... 128/869, 128/870, 872, 845, 876, DIG. 15; 602/60, 602/32, 33; 5/600, 621, 690, 628, 625; D29/100; D6/595

See application file for complete search history.

(56) References Cited

U.S. PATENT DOCUMENTS

| | | | | |
|---|---|---|---|---|
| 2,215,454 A | * | 9/1940 | Condit | 128/870 |
| 2,456,898 A | * | 12/1948 | Strandhagen | 128/870 |
| 4,854,305 A | * | 8/1989 | Bremer | 602/32 |
| 5,148,815 A | * | 9/1992 | Britton | 5/628 |
| 5,190,055 A | * | 3/1993 | O'Connor | 128/869 |
| 5,211,186 A | * | 5/1993 | Shoemaker et al. | 5/628 |
| 5,285,797 A | * | 2/1994 | Zeller | 5/628 |
| 5,875,781 A | * | 3/1999 | Klaus | 128/869 |
| 6,209,544 B1 | * | 4/2001 | Ek | 128/869 |
| 6,363,936 B1 | * | 4/2002 | McCormick et al. | 128/870 |
| 6,477,728 B1 | * | 11/2002 | Faz | 5/625 |

* cited by examiner

*Primary Examiner*—Fadi H. Dahbour
(74) *Attorney, Agent, or Firm*—Duckor Spradling Metzger & Wynne; Bernard L. Kleinke

(57) ABSTRACT

A device and method as disclosed relates to a bed mountable restraining device for confining a living being such as an infant, or a small animal, to a mattress of a bed. The device includes a base including a sheet of pliable material which is suitably sized to fit on the top surface of the mattress. A plurality of mounting straps are fixed to the base. An enclosure is attached to the base, whereby the adjustable straps may be releasably attached to the mattress by securing the straps over portions of the mattress.

20 Claims, 1 Drawing Sheet

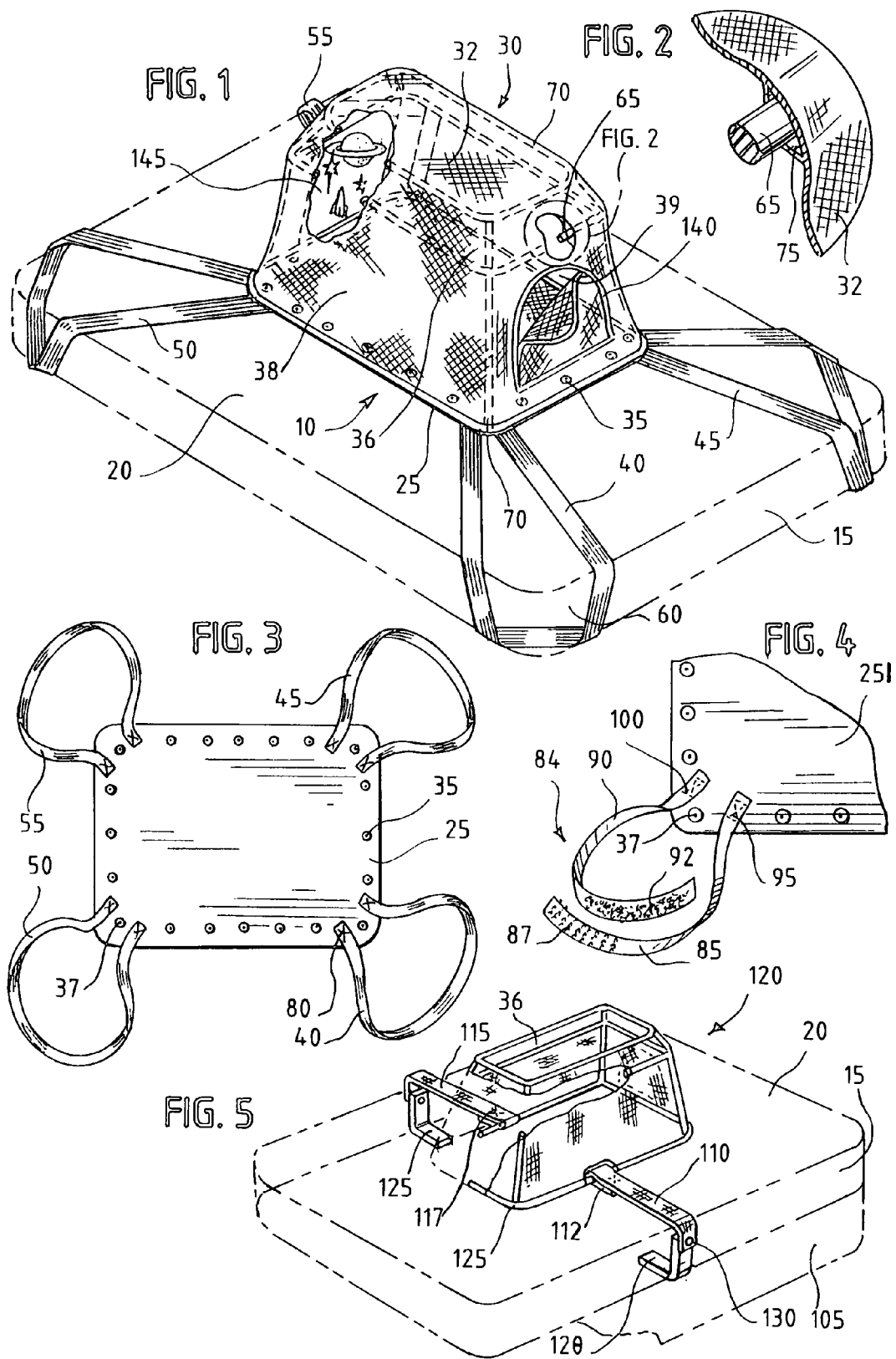

BED MOUNTABLE RESTRAINING DEVICE AND METHOD FOR USING SAME

FIELD OF THE INVENTION

The present invention relates in general to a bed mountable restraining device and method of using it. It more particularly relates to such a device and method for conveniently restraining a baby or an animal onto the top surface of a mattress on a bed.

BACKGROUND ART

There is no admission that the background art disclosed in this section legally constitutes prior art.

In the past, parents or other child care providers traveling to other people's homes or hotels with infants or small children would typically transport portable cribs or other restraining devices to confine their infants for purposes of sleeping or for conveniently playing in a secure area. These portable cribs or other restraining devices were not entirely convenient for some applications to transport due to their size, or weight, or their general lack of ease of portability. Alternatively, parents or child care providers who desire to travel with their infants and who desire to place their infants in a confined location would sometimes place the infants or small children on a bed and surround the infant with pillows. In this manner, the infant would be less likely to inadvertently roll off the bed and possibly sustain an injury.

BRIEF DESCRIPTION OF THE DRAWINGS

The features of this invention and the manner of attaining them will become apparent, and the invention itself will be best understood by reference to the following description of certain embodiments of the invention taken in conjunction with the accompanying drawings, wherein:

FIG. 1 is a partially broken away pictorial view of a bed mountable restraining device which is constructed in accordance with an embodiment of the invention and which is illustrated being attached to a bed mattress;

FIG. 2 is an enlarged scale fragmentary pictorial view of a detail portion including a support rod, mesh, and a seam of the device of FIG. 1;

FIG. 3 is a top plan diagrammatic view of a base and adjustable straps of the device of FIG. 1;

FIG. 4 is an enlarged scale top plan fragmentary view of another adjustable strap of a bed mountable restraining device, which is constructed in accordance with an alternative embodiment of the present invention; and FIG. 5 is a fragmentary pictorial view of a further bed mountable restraining device, which is constructed in accordance with yet another embodiment of the present invention, and which is illustrated being attached to a bed mattress.

DETAILED DESCRIPTION OF CERTAIN EMBODIMENTS OF THE INVENTION

It will be readily understood that the components of the embodiments as generally described and illustrated in the drawings herein, could be arranged and designed in a wide variety of different configurations. Thus, the following more detailed description of the embodiments of the system, components and method of the present invention, as represented in the drawings, is not intended to limit the scope of the invention, as claimed, but is merely representative of the embodiment of the invention.

A device and method as disclosed relates to a bed mountable restraining device for confining a person such as an infant, or a small animal, to a mattress of a bed. The device includes a base including a sheet of pliable material which is suitably sized to fit on the top surface of the mattress. A plurality of mounting straps are fixed to the base. An enclosure is attached to the base, whereby the adjustable straps may be releasably attached to the mattress by securing the straps over portions of the mattress.

According to one disclosed embodiment of the invention, a method is provided for using a bed mountable restraining device for confining a person such as an infant, or a small animal, on top of a mattress. The method includes using a base having an enclosure on top thereof and being formed of a sheet of pliable material having a plurality of straps fixed thereto for releasably attaching the base to the mattress. The base is placed onto the mattress and releasably secured to the mattress by extending the mounting straps over portions of the mattress. In one embodiment, the straps are formed into loops that may be slipped over corners of the mattress.

In certain embodiments, the enclosure has a top portion and a sidewall portion depending from the top portion and a cavity formed therein for placing the person or animal in the cavity. The infant or animal is placed onto the base and into the cavity of the enclosure, thereby conveniently confining the person or animal in place.

According to other embodiments, the mounting straps may be adjustable to accommodate different size mattresses such as standard, queen and king size.

Referring now to the drawings, and more particularly to FIG. 1 thereof, there is shown a bed mountable restraining device shown generally at 10, which is adopted to confine a person such as an infant (not shown), or a small animal (not shown), to a mattress 15 of a bed (not shown), and which is constructed in accordance with an embodiment of the invention. The device generally comprises a base 25 which may be generally rectangular in shape and formed of a washable, soft and pliable material such as plastic or cloth. The base 25 may be sized to fit within the boundaries of a top surface 20 of the mattress 15. The base 25 may have other shapes such as a circle or other shapes. The size and the shape of the base 25 may or may not be the same as the size and shape of the mattress.

An enclosure 30 is mounted on top of the base 25. The enclosure 25 may be composed of a semi-transparent and breathable mesh-type unwoven fabric material 32 which is preferably formed in the shape of a hollow rectangular block. It should be understood that a woven fabric may also be used. The enclosure 30 has a top portion 36 and a side wall portion 38 that depends from the top portion 36, thereby forming five of the six sides of a block. The sixth side or bottom side of the enclosure 30 is secured to the base 25 to complete an inner cavity 39 within the boundaries of the top portion 36 and the sidewall portion 38 of the enclosure 30. The cavity is sized to fit a small person or animal therein.

A woven or semi-transparent material 32 may be used so that the child care provider or pet owner may view the infant or animal restrained in the device 10. Moreover, the material 32 may be breathable (i.e., freely admit and dispense gases and breathable air) so that the living being (not shown) does not suffocate.

Continuing to reference FIG. 1, the base 25 may have a plurality of fasteners such as a two part snap fastener 35 spaced about its peripheral edges to secure releasably the base 25 to the side wall bottom peripheral edge portion 38 of the enclosure 30.

Other types and kinds of fasteners such as Velcro, slide fasteners and others may be employed. The base 25 thus may be releasably attached to the enclosure 30 so that the base 25 may be removed either for transportation or for cleaning or replacement. Also, the base 25 may be removed from the enclosure 30 to permit the person or animal to enter the device 10 as described hereinafter.

With continuing reference to FIG. 1, a plurality of adjustable straps such as adjustable loops 40, 45, 50, and 55 are attached to the base 25. These adjustable loops may be composed of an elastic type material which has the properties of being stretchable and are adapted to be stretched over mattress corners such as the mattress corner 60 of the mattress 15. As the adjustable loops 40, 45, 50, and 55 are adjustable and, as a result, they may be used to fit on various different sizes of mattresses. In this regard, the loops can stretch to increase the size of the loops to fit over large size mattresses. The elastic loops can snugly secure the base 25 to the mattress 15. Thus, the device 10 may be quickly and easily attached to the top surface 20 of the mattress 15 to secure the device 10 in place thereon, and yet be removable in a quick and easy manner without removing the covers (not shown) from the bed.

Although four adjustable straps are used on the device 10 as shown in FIG. 1, it should be appreciated that other configurations are possible that may use a fewer or greater number of straps. Also, the straps may be placed in other locations about the base 25. The straps may also be attached alternatively to the enclosure 30. Also, it will become apparent to those skilled in the art that the straps may not be adjustable and may be designed to fit a given size mattress only.

In operation, a child care provider, pet owner, or other person would place the base 25 centrally on the top surface 20 of the mattress 15. It should be appreciated that the base 25 may or may not already have the enclosure 30 releasably attached to the base 25 during the attachment of the base 25 to the bed mattress 15. The adjustable loops 40, 45, 50 and 55 extending from the base 25 are then stretched to increase their size to slip over the four corners, such as a corner 60 of the mattress 15 and then tucked underneath. Thus, the loop then snugly grips the corners under tension to apply opposing forces to all four corners of the base 25.

After the base 25 is releasably attached to the mattress 15, as described heretofore, the infant or animal is then placed on the base 25. If the enclosure 30 has already been attached to the base 25, then it would either be completely or partially detached from the base 25 to place the person or animal on the base 25, or preferably, the person or animal may be placed within the enclosure through an opening indicated at 39 and then a door 140 may be secured releasably thereover. After the person or animal is placed onto the base 25, the enclosure 30 is then completely releasably attached to the base 25 around their respective peripheral edges so that the infant or animal cannot readily escape from the device 10. This may be accomplished by connecting all of the snaps disposed on both the base 25 and enclosure 30, such as snap fastener 35.

When it is desired to remove the infant or animal from the device 10, the door 140 may be opened and the person or animal withdrawn through the opening 39. Alternatively, the enclosure 35 may be detached from the base 25 so that the person or animal may be removed therefrom. The device 10 may then be conveniently removed from the mattress 15 by untucking the attachment loops 40, 45, 50 and 55 from the mattress corners such as the mattress corner 60.

After the device 10 is removed from the mattress 15, the base may be completely removed from the enclosure means 30 so that it may be cleaned or stored. Furthermore, the components of the device 10 such as the base 25, the enclosure 30, and the adjustable loops 40, 45, 50 and 55 may be easily stored in a bag (not shown) or other convenient storage device (not shown) by folding or rolling the components to reduce their volume for subsequent storage or transportation as all of the components of the device 10 may be capable of being folded. This novel feature allows the device to be easily transported since the overall volume of the device may be substantially reduced in a compact manner. Moreover, the components of the device 10 may be light in weight to ease the burden to transport the device 10.

Considering now the enclosure 30 in more detail and with reference to FIG. 1, in order to provide structural support for the fabric material so that it generally forms the shape of a hollow inverted cup-shaped block, a plurality of collapsible support rods are connected to the fabric material 32. For example, a generally rectangular annular shaped support rod 65 is disposed in a horizontal plane about the periphery of the top portion 36 of the enclosure 30, thereby providing structural support thereto so that the enclosure 30 assumes the desired shape. Similarly, a smaller generally rectangular annular shaped support rod 70, is disposed horizontally spaced above the rectangular support rod 65 at the uppermost portion of the enclosure 30. Other support ribs or rods are disposed in an upright manner and join the horizontal rectangular rods 65 and 70 to help support the sidewall portions such as side wall portion 38 of the enclosure 30 to provide structural support thereto so that the enclosure 30 conforms to the desired shape. Other support rods (not shown) may also be strategically disposed about the fabric material 32 of the enclosure 30 to help provide structural support so that the enclosure 30 generally assume the desired shape to maintain its upright hollow configuration.

Considering now the support rods and their integration with the enclosure 30 in more detail and with reference to FIG. 2, the mesh non-woven fabric material 32 may include a seam 75 formed therein. The seam 75 may be adapted to receive a support rod such as the support rod 65 therein to secure the support rods to the fabric material. A plurality of seams and support rods may be strategically disposed about the mesh material 32 of the enclosure 30 as heretofore described so that the enclosure assumes the desired shape such as a cube as generally shown in FIG. 1.

It should be understood that there may be other techniques for attaching the support rods to the fabric material. Such techniques may include stitching, riveting, and others. Also, it should be understood that the fabric or other material may not be fixed to the support rods, and may, for example, merely rest on top of the support rods forming a support structure. Moreover, the walls of the enclosure 30 may be composed of rigid material such as sheets of rigid plastic material.

With reference now to FIG. 3, the base 25 and adjustable straps 40, 45, 50, and 55 of one embodiment of the invention, will now be considered in more detail. The base 25 may also be formed of an anti-microbial or hypoallergenic material. The mounting straps may be fixedly attached by stitching, such as stitching 80, or other attachment means such as adhesive, Velcro or other suitable techniques known in the art. The adjustable straps may also be integrally formed in the base 25.

Considering now the adjustable straps in more detail with reference to FIG. 3, the adjustable straps may be formed of an elastomeric material having the properties of being able to be stretched in length. This novel feature allows the base to be quickly and easily attached releasably to the top surface 20 of a mattress 15 about the corners thereof, such as the mattress corner 60 as best shown in FIG. 1.

In an alternative embodiment of the present invention and in reference to FIG. 4, a base 251 of another bed mountable restraining device constructed according to another embodiment of the invention, may incorporate an adjustable strap shown generally at 84. This alternative strap is similar to the strap 50, except the strap 85 is not stretchable but is adjustable in size. The strap 85 includes two separate substraps, such as substrap 85 and substrap 90 connected releasably and adjustably together at their ends to enable the strap 85 to be formed into an adjustable size loop which can accommodate different size mattresses.

Substrap 85 may be composed of a non-elastic material, although an elastic material may also be used for some applications. One end of the substrap 85 is stitched at 95 to the base 25 at one corner of the base 25. The opposite end of the substrap 85 may have fastening devices such as Velcro hooks disposed thereon, including Velcro hooks 87. Substrap 90 may also be formed of a non-elastic material. One end of the substrap 90 may be stitched proximate to the same corner of the base 25 that substrap 85 is stitched. The opposite end of substrap 90 may have fastening devices such as Velcro loops, including Velcro loop 92 deposited thereon. The Velcro loops 90 are adapted to releasably attach to the Velcro hooks 87.

With this structure, the effective size of the adjustable strap 84 may be modified by hooking the Velcro portion of substrap 85 to the desired position on the Velcro loop section of substrap 90 such that the size of the Velcro adjustable strap 84 is sized appropriately to be extended to and be tucked underneath a corner such as mattress corner 60 of the mattress 15 in a similar manner as the strap 50.

As best shown in FIG. 1, the door 140, may be formed in the mesh material 32 of the enclosure 30. The door may be designed to be opened and sealed by means of a suitable fastener such as a slide fastener, Velcro, or other. The door is provided so that the infant or animal may be placed within the cavity of the enclosure 30 on top of the base 25 without having to remove the enclosure 30 from the base 25 as described heretofore.

As shown in FIG. 1, an entertainment device 145 may be disposed on the inner surface of the enclosure 30. The entertainment device may be composed of pictures or other indicia that would be pleasing to either an infant or an animal placed within the bed mounted restraining device 10. The entertainment device 145 may be painted, stitched or otherwise attached to the mesh material 32 of the enclosure 30.

The cavity 38 in the enclosure 30 may be used to store either infant or pet supplies therein when the device 10 is transported. For this to occur, the enclosure 30 would not be collapsed so that the cavity 38 retains its volume to store supplies (not shown) therein.

Referring now to FIG. 5, there is shown a bed mountable restraining device 120, which is similar to the bed mountable restraining device 10 and which is constructed according to another embodiment of the invention. The device 120 is similar to the device 10, except a different technique is employed for attaching the device 120 to a mattress. The device 120 may be placed onto the top surface 20 of the mattress 15.

The device 120 includes a base 125, which may be similar to the base 20. In this embodiment, the mattress 15 is resting on a box spring 105 as is well known in the art.

A plurality of adjustable straps, such as adjustable straps 110 and 115, are provided. Each of the adjustable straps may be formed of a stretchable material such as an elastic material. However, it is to be understood that a non-stretchable material may also be employed. One end of each adjustable strap may be attached to the base 125 of the bed mountable restraining device 120 by looping the strap around a portion of the base 125 and securing it by using stitching, such as stitching 112. The base 125 may includes a slits or opening in the side walls of an enclosure forming a part of the device 120, to receive the adjustable straps, such as adjustable straps 110 and 115 at opposite sides thereof.

A plurality of L-shaped brackets, such as L-shaped bracket 128 and L-shaped bracket 125, may be connected to the ends of the straps, such as the strap 110. The L-shaped brackets each have two portions joined at 90 degree angles where one portion is adapted to fit between the mattress 15 and the box spring 105 and held between the mattress 15 and box spring 105.

The straps, such as the adjustable strap 110 is attached to the L-shaped bracket 120 through an attachment means, such as a snap, Velcro, or an adhesive as indicated at 130.

While the present embodiments of the invention disclosed herein have been particularly shown and described with reference to particular embodiments thereof, it will be understood by those skilled in the art that various changes in form and details may be made therein without departing from the true spirit and scope of the present invention.

What is claimed is:

1. A bed mountable restraining device for restraining a person or an animal to a mattress comprising:
    a base formed of a sheet of flexible and washable material sized to fit on the top surface of the mattress;
    a plurality of straps attached to the base for releasably attaching the base to the mattress;
    an enclosure releasably attached to the base, the enclosure having a top portion and a side wall portion depending from the top portion, and a cavity formed therein for receiving the person or animal within the cavity;
    the enclosure being constructed of a breathable and collapsible material having memory, wherein the enclosure means may be collapsed by applying selective pressure thereto thereby reducing the volume of the cavity; and
    wherein, the base is releasably attached to the mattress by placing the straps around portions of the mattress and the living being is placed onto the base and into the cavity of the enclosure means thereby restraining the living being by bounding the living being by the base and the top and side walls of the enclosure.

2. A bed mountable restraining device as recited in claim 1 further including
    a seam formed in the enclosure; and
    a support rod disposed in the seam for providing structural support to the enclosure.

3. A bed mountable restraining device as recited in claim 1 wherein the straps include an elastic material to be adjustable.

4. A bed mountable restraining device as recited in claim 1, wherein the straps further include Velcro.

5. A bed mountable restraining device as recited in claim 1, wherein the straps further include an L shaped bracket.

6. A bed mountable restraining device as recited in claim 1, wherein the straps are shaped to be tucked underneath the corners of the mattress.

7. A bed mountable restraining device as recited in claim 1, wherein four straps are attached to the base.

8. A bed mountable restraining device as recited in claim 1, wherein the enclosure is removably attached to the base through the use of snaps.

9. A bed mountable restraining device as recited in claim 1, wherein the enclosure is removably attached to the base through the use of Velcro.

10. A bed mountable restraining device as recited in claim 1, wherein the enclosure is formed of a semi transparent material for permitting viewing of the living being placed therein.

11. A bed mountable restraining device as recited in claim 1, wherein the enclosure further includes a door means formed therein for gaining access to the enclosure.

12. A bed mountable restraining device as recited in claim 1, wherein the enclosure further includes entertainment device for entertaining purposes placed therein.

13. A method of using a bed mountable restraining device for restraining a person or animal to a mattress, comprising:
    providing a base formed of a sheet of flexible and washable material having a plurality of adjustable straps attached thereto for releasably attaching the base to the mattress;
    placing the base onto the mattress;
    releasably securing the base to the mattress by placing the adjustable straps around a portion of the mattress;
    attaching an enclosure to the base, the enclosure having a top portion and a side wall portion depending from the top portion, and an cavity formed therein;
    the enclosure further being constructed of a breathable and collapsible material having memory wherein the enclosure means may be collapsed by applying selective pressure thereto thereby reducing the volume of the cavity; and
    placing the entire living being onto the base and into the cavity of the enclosure means thereby restraining the person or animal by bounding the living being by the base and the top and side walls of the enclosure means.

14. A method of using a bed mounted restraining device according to claim 13, further including expanding the enclosure before attaching the enclosure to the base.

15. A method of using a bed mounted restraining device according to claim 13, further including removing the person or animal from the device and then collapsing the restraining device for subsequent transportation or storage.

16. A method of using a bed mountable restraining device according to claim 13, further including opening a door means disposed in the enclosure means and having the living being traverse the door so that the living being is placed onto the base and into the cavity of the enclosure means.

17. A bed mountable restraining device for restraining a person or animal to a variably sized mattress comprising:
    means for providing a base formed of a sheet of flexible and washable material having a plurality of adjustable straps attached thereto for releasably attaching the base to the mattress;
    means for placing the base onto the mattress;
    means for releasably securing the base to the mattress by placing the adjustable straps around a portion of the mattress;
    means for attaching a enclosure to the base, the enclosure means having a top portion and a side wall portion depending from the top portion, and an cavity formed therein for placing the entire living being therein;
    the enclosure further being constructed of a collapsible and breathable material having memory wherein the enclosure means may be collapsed by applying selective pressure thereto thereby reducing the volume of the cavity; and
    means for placing the entire living being onto the base and into the cavity of the enclosure means thereby restraining the living being by bounding the living being by the base and the top and side walls of the enclosure means.

18. A bed mountable restraining device according to claim 17, further including means for expanding the enclosure before attaching the enclosure to the base.

19. A bed mountable restraining device according to claim 17, further including means for removing the person or animal from the device and then collapsing the restraining means for subsequent transportation or storage.

20. A bed mountable restraining device according to claim 17, further including means for fastening a door means disposed in the enclosure means and having the living being traverse the door so that the living being is placed onto the base and into the cavity of the enclosure means.

* * * * *